US00PP24077P2

(12) United States Plant Patent
Andrusiv

(10) Patent No.: US PP24,077 P2
(45) Date of Patent: Dec. 10, 2013

(54) ***BERBERIS* PLANT NAMED 'RED DREAM'**

(50) Latin Name: *Berberis thunbergii*
Varietal Denomination: Red Dream

(75) Inventor: Michal Andrusiv, Litomyal (CZ)

(73) Assignee: Valkplants B.V., Boskoop (NL)

( * ) Notice: Subject to any disclaimer, the term of this patent is extended or adjusted under 35 U.S.C. 154(b) by 97 days.

(21) Appl. No.: 13/506,332

(22) Filed: Apr. 13, 2012

(51) Int. Cl.
*A01H 5/00* (2006.01)

(52) U.S. Cl.
USPC ..... Plt./241

(58) Field of Classification Search
USPC ..... Plt./241
See application file for complete search history.

*Primary Examiner* — Susan McCormick Ewoldt
(74) *Attorney, Agent, or Firm* — Penny J. Aguirre

(57) ABSTRACT

A new cultivar of *Berberis*, 'Red Dream', that is characterized by its small sized leaves that are gray-purple to deep brown in color and its upright, broadly spreading plant habit with branches arching.

2 Drawing Sheets

Botanical classification: *Berberis thunbergii.*
Cultivar designation: 'Red Dream'.

RELATED APPLICATIONS

This application is co-pending with U.S. Plant Patent applications filed for cultivars derived from the same breeding program entitled *Berberis* Plant Named 'Orange Dream' (U.S. Plant application Ser. No. 13/506,333) and *Berberis* Plant Named 'Golden Dream' (U.S. Patent application Ser. No. 13/506,337).

BACKGROUND OF THE INVENTION

The present invention relates to a new and distinct cultivar of *Berberis thunbergii*, and will be referred to hereafter by its cultivar name, 'Red Dream'. 'Red Dream' is grown for use as a landscape shrub.

The new cultivar arose through an ongoing breeding project by the Inventor in Litomysl, Czech Republic with the objective of selecting new and unique cultivars of *Berberis*. 'Red Dream' arose from open pollination in 2003 of an unnamed plant of *Berberis thunbergii* from the Inventors breeding program as the female parent. 'Red Dream' was selected as a single unique plant from the resulting seedlings in 2005.

Asexual reproduction of the new cultivar was first accomplished by the Inventor by softwood stem cuttings in Litomysl, Czech Republic in 2007. It has been determined that the characteristics of this cultivar are stable and are reproduced true to type in successive generations.

SUMMARY OF THE INVENTION

The following traits have been repeatedly observed and represent the characteristics of the new cultivar, which in combination distinguish 'Red Dream' as a new and distinct cultivar of *Berberis.*

1. 'Red Dream' exhibits small sized leaves.
2. 'Red Dream' exhibits foliage that is gray-purple to deep brown in color.

3. 'Red Dream' exhibits on upright, broadly spreading plant habit with branches arching.

The female parent of 'Red Dream' differs from 'Red Dream' in having dark green leaves, a more open growth habit, and broader and larger leaves. 'Red Dream' can be most closely compared to the cultivars 'Orange Dream', 'Golden Dream' 'Admiration' (U.S. Plant Pat. No. 16,921), and 'Aurea' (not patented). 'Golden Dream' differs from 'Red Dream' in having yellow-green leaves, a more compact plant habit, and branches that are upright rather than branching. 'Orange Dream' differs from 'Red Dream' in having leaves that are less deep brown in color. 'Admiration' differs from 'Red Dream' in having broader larger leaves that are gray-purple to orange-brown in color with thin yellow-green margins and in having a more compact dense plant habit. 'Aurea' differs from 'Red Dream' in having yellow leaves and a more compact plant habit.

BRIEF DESCRIPTION OF THE DRAWING

The accompanying colored photographs illustrate the overall appearance and distinct characteristics of the new *Berberis*. The photographs were taken of a plant two years in age as grown in a one-gallon container in Helden, The Netherlands.

The photograph in FIG. 1 provides a view of the plant habit of 'Red Dream' and the photograph in FIG. 2 provides a close-up view of the foliage of 'Red Dream'.

Figure 1:
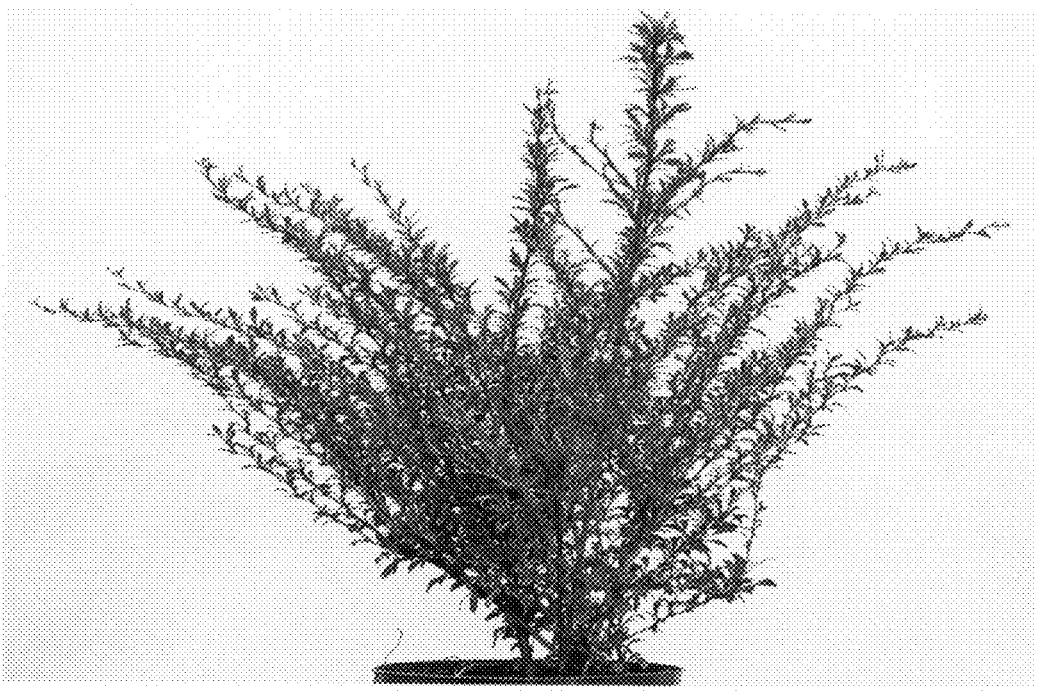
Figure 2:
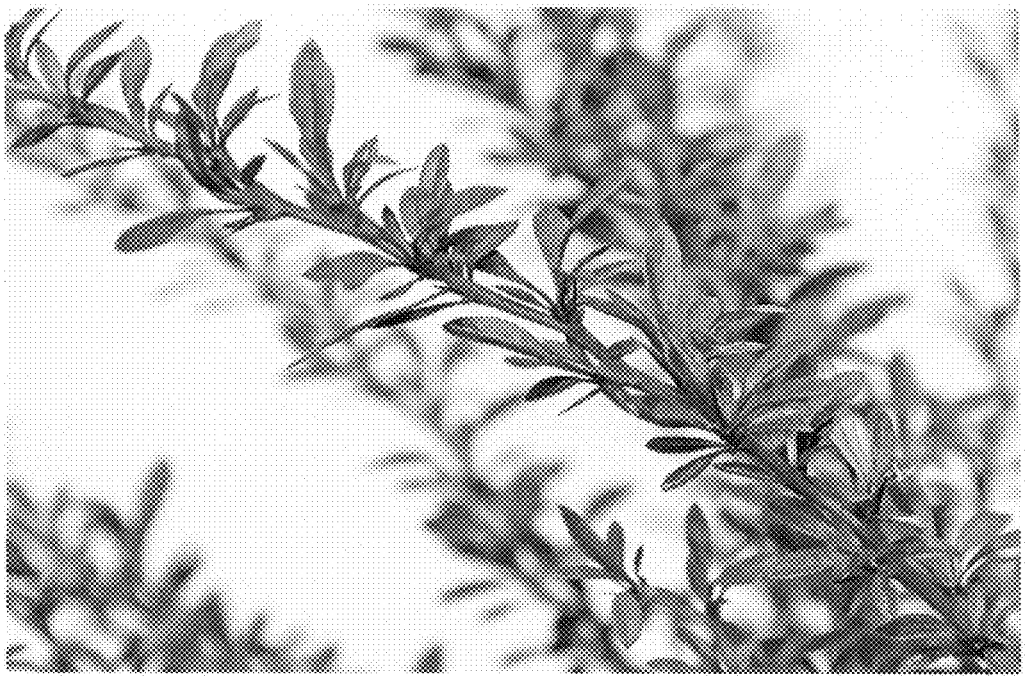

The colors in the photographs may differ slightly from the color values cited in the detailed botanical description, which accurately describe the colors of the new *Berberis.*

DETAILED BOTANICAL DESCRIPTION OF THE PLANT

The following is a detailed description of two year-old plants of the new cultivar as grown in one-gallon containers in Helden, The Netherlands. Plants were grown under average day temperatures of 15° C. and average night temperatures of 10° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type.*—Perennial deciduous shrub.

*Plant habit.*—Broad upright spreading, flattened globular in shape.

*Height and spread.*—Reaches about 35.8 cm in height and 58.3 cm in width in a one-gallon container.

*Cold hardiness.*—Hardy to at least U.S.D.A. Zone 5.

*Disease resistance.*—Not more susceptible to pests and diseases than other *Berberis.*

*Root description.*—Fibrous, moderate to densely branched.

*Growth rate.*—Moderate.

*Propagation.*—Softwood stem cuttings.

*Rooting.*—Initiate in 28 to 36 days at 17° C. air temperature, a young fully rooted plant is produced in 28 to 36 days at 17 to 19° air temperature (summer).

Stem description:

*Stem size.*—Lateral branches are an average of 24.8 cm in length and 2 mm in diameter.

*Stem shape.*—Round.

*Stem color.*—Young shoots; 184A to 184B, later turning 178A to 178B, under side; N199D, mature stems; between 200B and N200B.

*Stem surface.*—Young and mature stems (both sides) moderately glossy and axially ribbed.

*Stem strength.*—Strong.

*Internode length.*—Average of 8 mm.

*Branching habit.*—Moderate to high with an average of 70 lateral branches.

*Branching aspect.*—Lateral branches an average angle of 40° (vertical=0°), branch tips an average angle of 10° due to arching of branches.

Foliage description:

*Leaf shape.*—Oblanceolate to obovate.

*Leaf division.*—Simple.

*Leaf base.*—Long attenuate.

*Leaf apex.*—Broad acute with a small (not sharp) mucronate tip.

*Leaf venation.*—Pinnate.

*Leaf margins.*—Entire.

*Leaf attachment.*—Sessile.

*Leaf arrangement.*—Alternate, clustered.

*Leaf surface.*—Upper surface; smooth and slightly glossy, lower surface; dull.

*Leaf color.*—Upper surface immature foliage; between N186C and 200B, lower surface immature foliage; between N187C and N200B, mature foliage upper surface; between N186C and 200A, leaves at base of lateral branches in the shade ("inside" the plant) turn N137B, slightly tinged N200A, mature lower surface foliage; 137C, leaves at base of lateral branches in the shade ("inside" the plant) turn 147B, very slightly tinged between N186B and N200B.

*Leaf number.*—Average of 7 per cluster at each node, 210 leaves per lateral branch.

*Leaf size.*—Average of 2 cm in length and 0.4 cm in width.

*Leaf aspect.*—Held upward at about a 45° angle.

*Leaf veins.*—Upper surface; 146C, lower surface; 146B to 146C.

*Petioles.*—No petioles present, leaf bases long attenuate.

*Thorn.*—Below each node is a sharp single thorn; average of 5 mm length and 1 mm in width at base, color; upper side; N170B, tip; 200B, mature thorns; 200A.

Flower description:

*Flowering.*—No flowers have been observed.

*Fruit and seed.*—Seed production has not been observed.

It is claimed:

1. A new and distinct cultivar of *Berberis* plant named 'Red Dream' as herein illustrated and described.

* * * * *